United States Patent [19]

Friese et al.

[11] 4,428,747

[45] Jan. 31, 1984

[54] TAMPON BLISTER PACK

[76] Inventors: Axel Friese, Weststrasse 68, D-5600 Wuppertal, Fed. Rep. of Germany; Stefan Simon, Herzfelderstrasse 9, A-2351 Wiener Neudorf, Austria

[21] Appl. No.: 305,636

[22] PCT Filed: Feb. 4, 1981

[86] PCT No.: PCT/DE81/00027

§ 371 Date: Sep. 21, 1981

§ 102(e) Date: Sep. 21, 1981

[87] PCT Pub. No.: WO81/02251

PCT Pub. Date: Aug. 20, 1981

[30] Foreign Application Priority Data

Feb. 5, 1980 [DE] Fed. Rep. of Germany ....... 3004164

[51] Int. Cl.$^3$ ............................................. A61F 13/20
[52] U.S. Cl. .................................................. 604/12
[58] Field of Search ....................... 128/285, 263, 270; 206/210, 220, 225, 229, 529, 531, 532, 581, 438, 823; 604/11-12, 14

[56] References Cited

U.S. PATENT DOCUMENTS

| | | | |
|---|---|---|---|
| Re. 29,705 | 7/1978 | Compere | 206/532 |
| 2,530,127 | 11/1950 | Kubik | 206/529 |
| 2,613,011 | 10/1952 | Foreshaw-Smith | 206/823 |
| 3,335,726 | 8/1967 | Maranto | 128/270 |
| 3,358,686 | 12/1967 | Asaka | 128/270 |
| 4,198,171 | 4/1980 | Lampka et al. | 206/229 |
| 4,271,835 | 6/1981 | Conn et al. | 128/270 |

Primary Examiner—C. Fred Rosenbaum
Assistant Examiner—Sherri Vinyard
Attorney, Agent, or Firm—Jason Lipow

[57] ABSTRACT

A blister package, particularly for sanitary tampons (3) for women hygiene, is comprised of a pressed foil (1) forming a deep hollow and of a cover foil, and comprises a deposit (6) for an additive, preferably a lubricant. The deposit (6) is arranged in a main trough (19) intended to receive the sanitary tampon (3). The deposit (6) may be shaped as a cup (5) of the pressed foil (1) and opened in the hollow of the pressed foil (1) or be covered or separated from the main trough (19). The deposit (6) may be relieved through the opening of the blister package and brought in contact with the end (3a) and the pad (3), but the deposit may also be pressed by means of the finger applied pressure in the direction of the end (3a) of the pad (3) to coat it before the opening of the blister package and the use of the pad (3). The additive will therefore be applied immediately before using the sanitary tampon, so that all of the amount of additive available achieve its purpose.

5 Claims, 17 Drawing Figures

TAMPON BLISTER PACK

The invention relates to a tampon blister pack, particularly for female hygiene.

In some cases it is desirable or necessary in connection with tampons which are suitable in particular for female hygiene to use active substances which either facilitate the application of the tampon or are to fulfill therapeutic or diagnostic purposes. Thus, the introduction of tampons, for example, causes discomfort, in particular when the period is subsiding. Because insufficient moisture is then present, sliding of the tampon is impeded by the friction between the walls of the organ and the outer surface of the tampon.

It is known to coat tampons, and particularly the rounded introduction ends of such tampons, with active substances, such as lubricants or pharmaceutical substances for therapy or diagnosis. However, a tampon which has been coated in this way a long time before use can have the disadvantage that the active substance applied to the tampon is absorbed in the course of time by the highly absorbent tampon and that there is thus the danger that the purpose intended with the active substance will not be achieved. It is furthermore known to surround tampons with a solid substance which penetrates the tampon to a very small extent or even not at all. These tampons have the disadvantage that the rate of absorption is severely restricted by the closed coating. In the case of intermittent bleeding there is then a risk of the secretion flowing past the non-expanded tampon.

The invention is therefore based on the problem to provide a tampon blister pack, in particular for female hygiene, of such a design that the active substance, preferably a lubricant, is applied to the tampon, in particular to its front zone, only immediately before use so that substantially the entire amount of the present active substance will be available for the purpose to be achieved.

This problem is solved by the invention by a depot located at a distance from the tampon. The depot can be arranged in a cup of the deep-drawn film which in the area of the main deep-drawn film is open or covered or is arranged separate from the latter. The depot can be uncovered by opening the blister pack and then be brought into contact with the introduction end of the tampon, or it can be squeezed out by finger pressure in the direction of the introduction end of the tampon and be applied thereto before opening the blister pack and using it.

The features of the tampon blister pack according to the invention can be seen from the patent claims.

In the following text, preferred embodiments of the tampon blister pack according to the invention are explained by reference to the drawings in which.

Figure 1:
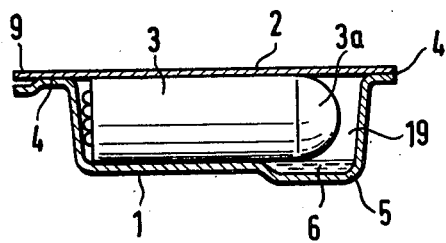
FIG. 1 shows a longitudinal section of a tampon blister pack having an open cup provided in the deep-drawn film and containing the depot.

FIG. 1 shows a blister pack, consisting of a deep-drawn film 1 and a cover film 2. A tampon 3 is arranged in a main deep-drawn recess 19. The seal face between the deep-drawn film 1 and the cover film 2 is marked by the reference numeral 4. An open cup 5 which contains the lubricant depot 6 is provided in the deep-drawn film 1. The cup 5 is located in the zone of the rounded insertion end 3a of the tampon 3, at a clear distance from the latter. This ensures that the tampon 3 does not prematurely come into contact with the lubricant depot 6. Of course, it is possible also to provide the lubricant cup in the zone of the rear end of the tampon or in the middle zone of the tampon. The arrangement of the lubricant depot 6 in the zone of the insertion end of the tampon 3 is however preferred, since a reliable immersion, without problems, of the insertion end of the tampon 3 into the lubricant depot 6 is to be ensured even if the tampon is put into use under conditions of poor light.

Figure 2:
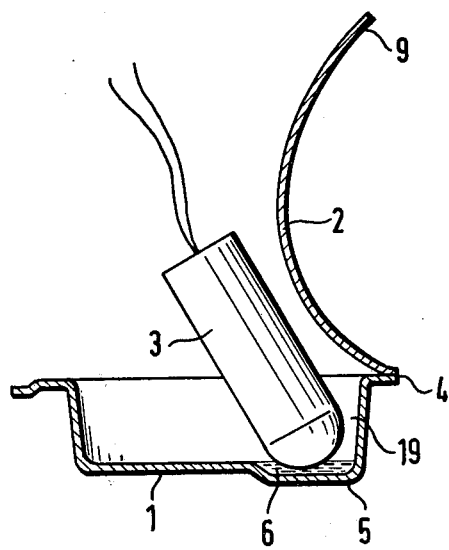
FIG. 2 shows a longitudinal section of the pack in FIG. 1, the tampon being immersed in the cup with the depot.

FIG. 2 shows the tampon pack of FIG. 1 in the opened position, the tampon 3 being immersed into the open lubricant cup 5 in order to transfer the lubricant onto the insertion end of the tampon.

Figure 3:
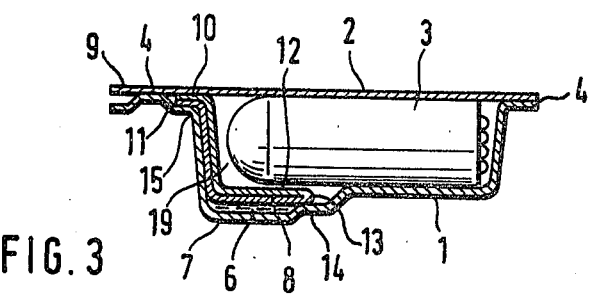
FIG. 3 shows a longitudinal section of a tampon blister pack having a covered depot cup in the deep-drawn film.
Figure 4:
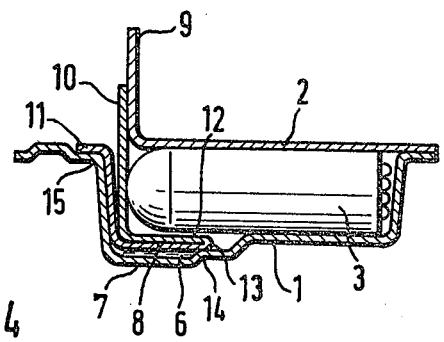
FIG. 4 shows a longitudinal section of the pack in FIG. 3, at the start of the opening phase.
Figure 5:
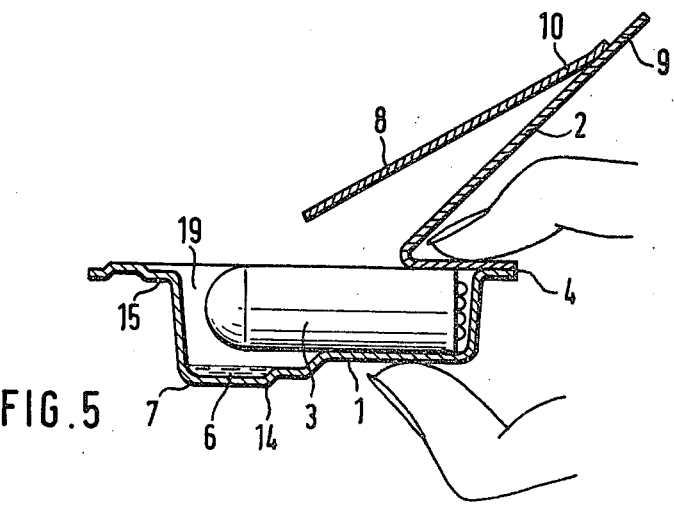
FIG. 5 shows a longitudinal section of the pack in FIG. 3 in the opened position.

In the embodiment according to FIG. 3, having a lubricant cup 7, the lubricant depot 6 is covered by an interleaf 8 which is transversely folded at 13. The free ends 10 and 11 of the interleaf 8 rest on a shoulder 15, which is sunk relative to the seal face 4, of the deep-drawn film 1. The free end 10 of the upper ply is sealed to the cover film 2 and the free end 11 of the lower ply is sealed to the shoulder 15. The free end 10 of the upper ply is more strongly sealed on than the free end 11 of the lower ply so that, when the cover film 2 is torn open by lifting the gripping tab 9, the seal of the end 11 is detached and the interleaf 8 is automatically pulled out in the manner shown in FIGS. 4 and 5. FIG. 5 shows the way in which the user grips the tab. This shows that the tampon remains in the packaging when the latter is opened. While the pack is closed, the end of the cover leaf 8, formed by the transverse fold 13, rests on a shoulder 14 which is sunk relative to the main plane of the deep-drawn film 1, the upper edge 12 of the upper ply being flush with the main plane of the deep-drawn film 1. The end with the transverse fold 13 can be lightly sealed to the shoulder 14, in which case this seal must also be more readily detachable than the seal of the free end 10 to the cover film 2. After the cover film 2 has been lifted off with simultaneous removal of the interleaf 8, the tampon 3 can be taken out and its insertion end can be immersed in the lubricant depot 6.

Figure 6:
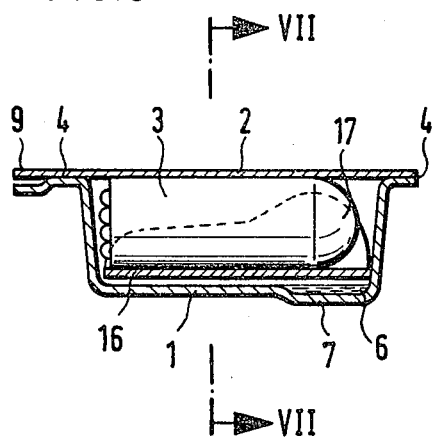
FIG. 6 shows a longitudinal section of a tampon blister pack having an asymmetrical interleaf located between the bottom of the deep-drawn film and the tampon.
Figure 7:
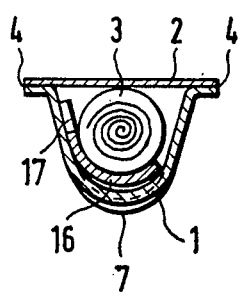
FIG. 7 shows a cross-section along the line VII—VII of FIG. 6.

FIGS. 6 and 7 show a tampon blister pack with a lubricant cup 7 similar to that illustrated in FIG. 3. Between the tampon 3 and the bottom of the deep-drawn film 1, there is a loose interleaf 16 which ensures covering of the lubricant depot 6. The end of the interleaf 16, which is adjacent to the insertion end of the tampon in the form of a rounded head, is widened one one longitudinal side of the tampon approximately up to half the height of the over film 2 and forms at that point a gripping tab 17 which makes it easier to pull out the interleaf 16 after the cover film 2 has been opened. Subsequently, the tampon 3 can be immersed in the lubricant depot 6 as described.

Figure 8:
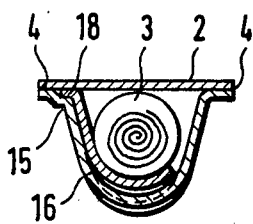
FIG. 8 shows a cross-section of a tampon blister pack having an interleaf which is drawn up on one longitudinal side of the tampon up to the cover film.

The end 18, adjacent to the insertion end of the tampon, of the interleaf shown in FIG. 8 is drawn up on one longitudinal side of the tampon up to the cover film 2 and is sealed to the cover film 2. Preferably, the end 18 rests in a sunk shoulder 15 of the deep-drawn film 1 in a manner similar to that explained above with reference to FIG. 3. When the cover film 2 is opened, the sealed-on interleaf 16 is automatically pulled out.

Figure 9:
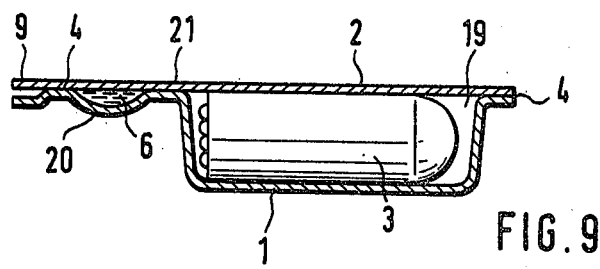
FIG. 9 shows a longitudinal section of a tampon blister pack in which a cup for the depot is separated from a deep-drawn recess for the tampon.
Figure 10:
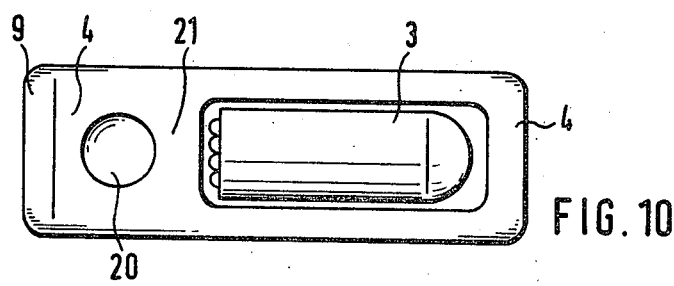
FIG. 10 shows a plan view of the pack in FIG. 9.
Figure 11:
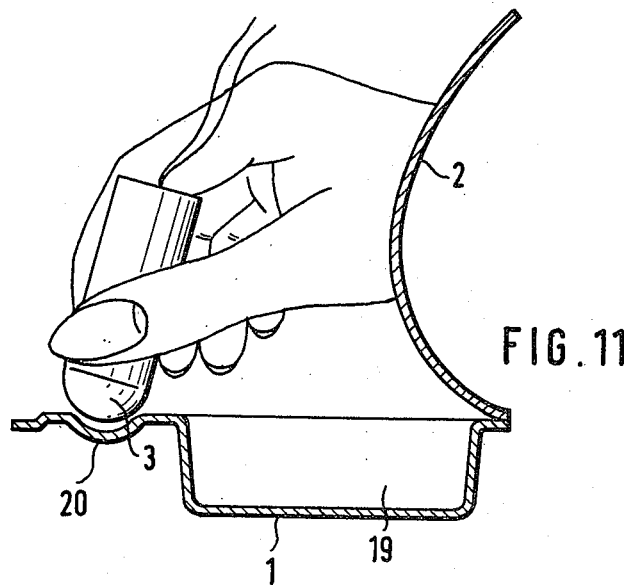
FIG. 11 shows a longitudinal section of the pack in FIG. 9 in the opened position, the tampon being immersed into a cup.

FIG. 9 shows a particulary preferred embodiment of a tampon blister pack. The lubricant depot 6 is located in a cup 20 of the deep drawn film 1 which is separated from the main deep-drawn recess 19 for the tampon 3, preferably by a tight seal face 21. After the cover film has been stripped off, the tampon 3 is immersed in the lubricant depot 6, as shown in FIG. 11. The separation of the deep-drawn recess 19 from the cup 20 for the lubricant depot 6 and the tampon 3 has the advantage that, from the point of view of packaging technology, there are no particular demands on viscosity of the lubricant. This embodiment can be manufactured with a particularly small expenditure of time and machines.

Figure 12:
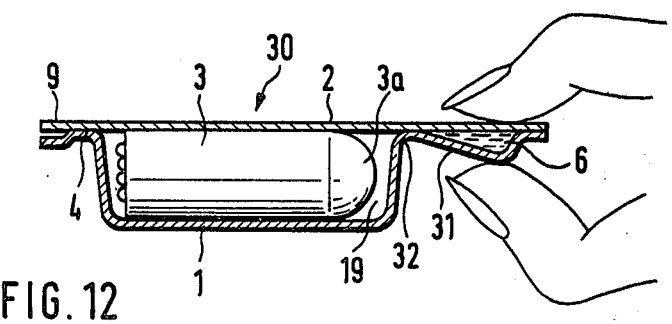
FIG. 12 shows a longitudinal section of a further embodiment of a tampon blister pack having a gripping tab designed as depot.
Figure 13:
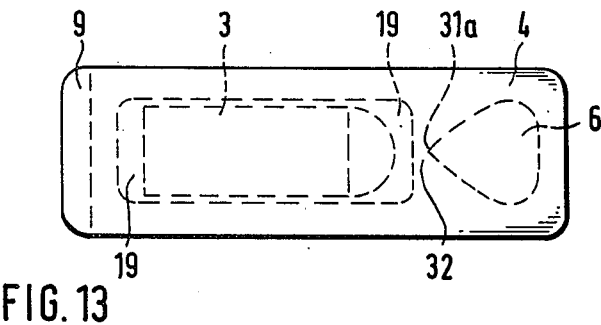
FIG. 13 shows a plan view of the blister pack according to FIG. 12.

In FIGS. 12 and 13 a tampon blister pack 30 is shown in which the main deep-drawn recess 19 for receiving the tampon 3 is separated from a cup 31, which according to FIG. 13 is heart-shaped in cross section, by a web 32 which is tightly connected to the cover film 2, however less tightly than the remaining sealing face 4 of the deep-drawn film. The welded joint of the web 32 of the deep-drawn film 1 with the cover film 2 is made weaker to such extent that by squeezing together the depot 6 by exerting finger pressure on the cover film 2 and the cup 31, according to FIG. 12, the connection between cover film 2 and web 32 is destroyed in the zone of the tip 31a and a connecting passage is consequently formed at the narrowest point of the web 32 between the cup 31 and the main deep-drawn recess 19. By this, a hygienically unobjectionable application of the lubricant onto the rounded insertion end 3a of the tampon is achieved since under no circumstances the user comes into immediate contact with the lubricant. After that, the user can open the blister pack by seizing the gripping tab 9 of the cover film 2 and take the tampon, wetted with the lubricant, out of the pack for use.

Figure 14:
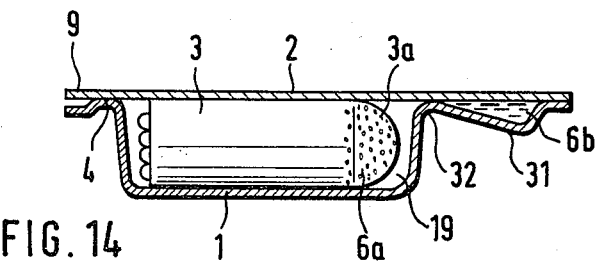
FIG. 14 shows a longitudinal section according to FIG. 12 with a coating of the rounded introduction end of the tampon with a powdery component and a filling of the cup with a liquid component of a lubricant.

The embodiment according to FIG. 14 differs from that shown in FIGS. 12 and 13 merely in that the insertion end 3a of the tampon is coated with a powdery component 6a of the lubricant from the beginning, while the cup 31 contains in this case a liquid component 6b of the lubricant which is pressed or sprayed on the powdery substance on the insertion end of the tampon in the manner described above, namely by squeezing together the cup 31 and the cover film thereon, expediently before putting the tampon into use, so that both components of the lubricant are combined to a lubricant, facilitating insertion, shortly before the tampon is introduced in the body.

Figure 15:
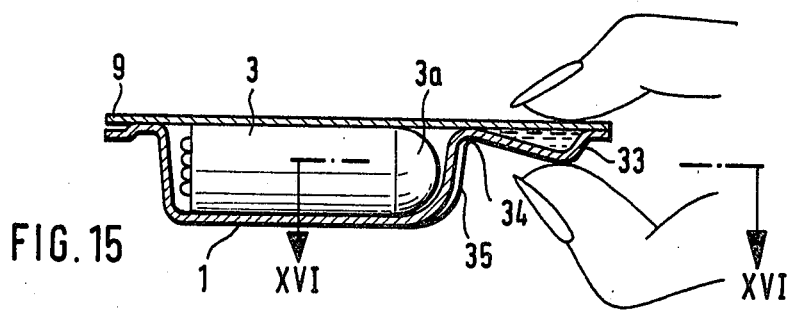
FIG. 15 shows a longitudinal section of a further modified embodiment of the tampon blister pack.
Figure 16:
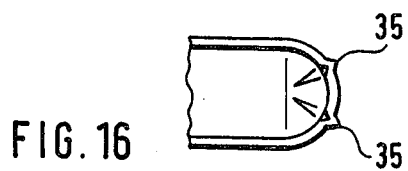
FIG. 16 shows a section according to line XVI—XVI in FIG. 15.
Figure 17:
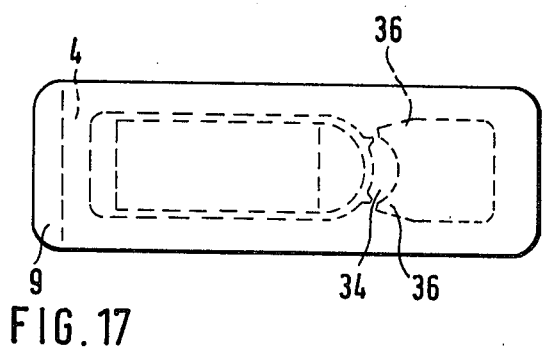
FIG. 17 shows a plan view of the pack according to FIG. 15.

The embodiment according to FIGS. 15 to 17 differs from that according to FIGS. 12 to 14 substantially by a modified design of a cup 33 and a web 34 between the cup 33 and the main deep-drawn recess 19 which in the present case is more closely adapted in its length to that of the tampon 3 so that the tampon has almost no play in the longitudinal direction.

As shown in particular by FIG. 17, the deep-drawn film 1 comprises two grooves 35 which extend from the web 34 in the wall of the main deep-drawn recess 19 opposite the insertion end 3a to approximately the bottom of the main deep-drawn recess and are increasingly tapered towards the latter. These grooves 35 are located opposite each other in corners 36 of the cup projecting in the direction of the main deep-drawn recess 19 and on the respective smallest width of the web 34 such that, upon a compression, the lubricant can be applied onto the insertion end 3a before the gripping tab is seized for opening the pack.

The dimension of the cup 31 or 33, respectively, is, according to FIGS. 13 and 17, made such, that, when seen in cross-section, the cup is substantially completely covered by the finger of a user.

It is a matter of course that in the embodiment of FIGS. 12–17 the connection between the cover film and the web of the deep-drawn film is made less strong than the tensile strength of the cover film so that a bursting of the cover film is under all circumstances prevented when a compression is exerted on the cup and the cover film. The grooves 35 are formed simultaneously with the deep-drawing of the deep-drawn film for forming the main deep-drawn recess 19 and the cup 33. The lubricant component which is applied to the tampon may be in the form of a thin gelatin film which, prior to the putting into use is wetted by the depot liquid and thereby develops the desired viscosity. The liquid may be provided in the depot also in a capsulated form, whereby, for example, a drying out of the depot can be prevented.

The lubricants which can be used are bio-compatible lubricants which impart an adequate slipperiness to the tampon. The consistency of the lubricants is such that, especially in the case of an open cup, the lubricant retains its form and position even on prolonged storage and temperatures of about 30° C. The following substances can be used as lubricants or for the lubricant composed as two-component system, alone or in mixture: extracts of sea algae, such as alginates, agar, carrageen; exsudates of plants, such as tragacanth, gum arabic; extracts of plants, such as pectins; starch fractions and derivates, such as dextrins, amylopectins, hydroxy ethyl starch; derivates of cellulose, such as methyl, ethyl, and hydroxypropyl cellulose; fatty substances, such as mono, di, triglycerides of higher saturated fatty acids, polyalkylene glycols and other ethoxylated products, such as polyethylene glycol 200–4000, PEG-6-capryl/caprine glyceride; hydrocarbons, such as paraffin oils, vaseline; polymers, such as polyvinyl alcohols, polyvinyl pyrrolidones, polyacrylates; alcohols, such as ethylene glycol, glycerol; emulsifiers, such as lecithin, cholesterin, or derivates of the sorbitan fatty acid esters. If desired, these lubricants can contain additives, such as plasticizers, solvents, preservatives and the like.

Of course, the depot may consist also of pharmaceutical preparations or diagnostics which are to be introduced in the body cavity only shortly before putting into use a tampon and together with the latter.

We claim:

1. In combination, a tampon and a tampon blister pack for containing said tampon and a substance to be applied to the tampon prior to use comprising:
   a continuous deep drawn film comprising a first chamber containing said tampon and a second chamber for providing a depot for said substance;
   said chambers being spaced apart to preclude contact between said tampon and said substance prior to use;
   a single cover film overlying said continuous deep drawn film and preventing access to both of said chambers until said cover film is removed.

2. The tampon blister pack of claim 1 wherein said first chamber comprises a main deep drawn recess in said deep drawn film and said second chamber comprises an open cup formed by a second recess in said drawn film below said main recess.

3. The tampon blister pack of claim 2 wherein said second chamber is separated from said first chamber by an interleaf sealed over said second chamber and said interleaf is affixed to said cover film; the affixation of said interleaf to said cover film being stronger than the seal of said interleaf over said second chamber; whereby when said cover film is removed, said seal over said second chamber is broken exposing both said chambers.

4. The tampon blister pack of claim 1 wherein said first chamber is formed by a deep drawn recess in said deep drawn film and said second chamber is formed by a second recess in said drawn film; said chambers being separated by an unrecessed portion of said drawn film with said cover film being sealed to the periphery of both recesses and the unrecessed portion of said drawn film to enclose the tampon and the substance within their respective chambers and separate them from each other prior to removing said cover film.

5. The tampon blister pack of claim 1 wherein said seal between said cover film and the chambers is sufficiently weak whereby finger pressure applied to the second chamber is sufficient to break said seal and cause said substance to be contained in said second chamber to flow into said first chamber.

* * * * *